United States Patent
Liu

[11] Patent Number: 6,030,861
[45] Date of Patent: Feb. 29, 2000

[54] METHOD FOR FORMING DUAL-GATE CMOS FOR DYNAMIC RANDOM ACCESS MEMORY

[75] Inventor: Jiann Liu, Irving, Tex.

[73] Assignee: Texas Instruments Incorporated, Dallas

[21] Appl. No.: 09/001,051

[22] Filed: Dec. 30, 1997

Related U.S. Application Data

[60] Provisional application No. 60/034,594, Jan. 2, 1997.

[51] Int. Cl.$^7$ ............................................... H01L 21/8238
[52] U.S. Cl. ........................................................ 438/217
[58] Field of Search .................................. 438/587, 217, 438/275, 289

[56] References Cited

U.S. PATENT DOCUMENTS

| | | | |
|---|---|---|---|
| 4,658,220 | 4/1987 | Heston et al. | 330/277 |
| 5,384,724 | 1/1995 | Jagini | 364/770 |
| 5,550,079 | 8/1996 | Lin | 437/56 |
| 5,563,093 | 10/1996 | Koda et al. | 437/101 |
| 5,747,368 | 5/1998 | Yang et al. | 438/217 |
| 5,851,865 | 12/1998 | Koike | 438/217 |

*Primary Examiner*—Joni Chang
*Attorney, Agent, or Firm*—W. James Brady III; Richardson L. Donaldson

[57] ABSTRACT

A method for forming a dual-gate transistor includes the step of forming a gate oxide layer (18) over two transistor regions provided by a P-tank (12) and an N-tank (14). This is followed by depositing a layer of in-situ doped poly (20) and then masking off a portion of the poly layer (20) overlying the P-tank (12). This is then followed by diffusion of P-type impurities into the portion of the poly layer (20) overlying the N-tank (14) associated with the P-channel transistor. This is a process required for forming a DRAM memory. Utilizing the same oxide mask (22), a threshold implant is formed into the N-type (14).

7 Claims, 2 Drawing Sheets

METHOD FOR FORMING DUAL-GATE CMOS FOR DYNAMIC RANDOM ACCESS MEMORY

This application claims priority under 35 USC § 119(e) (1) of provisional application No. 60/034,594 filed Jan. 2, 1997.

TECHNICAL FIELD OF THE INVENTION

The present invention pertains in general to a method for manufacturing a semiconductor device having a common MOSFET with both an N-channel MOSFET and a P-channel MOSFET on the same substrate, and in particular, the method of manufacturing a dual-gate CMOS device.

BACKGROUND OF THE INVENTION

Typically, the gate electrode of complimentary MOSFETs has been formed by patterning a layer of polysilicon after doping thereof by ion implantation and/or solid-phase diffusion of N-type impurities, such as phosphorous or arsenic. Typically, the gate electrode will be disposed over two separate regions, a P-type region and an N-type region. The P-type region is utilized to form N-channel transistors and the N-type region is utilized to form P-channel transistors. These are typically referred to as a P-tank and an N-tank. In this prior art system, the gate electrodes for both the N-channel transistors and the P-channel transistors are of N-type with the source/drain regions in the N-channel transistor being N-type and the source/drain regions in the P-channel devices being P-type.

As the channel regions decrease in width as a result of the finer photolithography techniques and processes that are currently in use, the gate electrode for the P-channel transistor have been doped with a P-type impurity in order to suppress the short channel effect. In order to accomplish this, it is necessary to dope the polysilicon layer from which the gate electrodes are formed with both N-type impurities and P-type impurities. One system that has been proposed for achieving this is to utilize some type of mask and dope N-type impurities in the portion of the polysilicon layer overlying the P-type tank and then masking off this portion of the substrate and exposing the portion of the polysilicon layer overlying the N-tank and doping it with P-type impurities. Thereafter, the gate is patterned in the poly layer and underlying gate oxide layer and source/drain implants formed on either side of the gate in both the P-tank and the N-tank. In some cases, the source/drain implants and the implants into the gate electrodes are performed at the same time. In another technique for doping the gate electrodes for both transistors provides for some type of diffusion barrier between the gate electrodes for the N-channel and P-channel transistors, especially when the gate electrodes are formed from a common strip of polysilicon. This barrier can be formed from some type of nitride such as a metal nitride layer. However, the step of initially providing the N-doped and P-doped regions of polysilicon to form the gate electrodes for the N-channel and P-channel transistors requires a number of different steps. This can create a problem due to the additional thermal cycles that are required.

SUMMARY OF THE INVENTION

The present invention disclosed and claimed herein comprises a method for forming a gate electrode for a dual-gate CMOS transistor utilized in a DRAM. First and second transistor regions of first and second and opposite conductivity types, respectively, are first formed, these transistor regions being the regions in which transistors are to be formed. A gate oxide layer is then disposed over the surfaces of the first and second transistor regions and then a layer of conductive material is formed over the first and second regions and above the gate oxide layer, which layer of conductive material has disposed therein in-situ dopants of the first conductivity type. The upper surface of the layer of conductive material is then masked such that the portion overlying the second transistor region of the second conductivity type is masked. Second conductivity type dopants are then introduced into the unmasked portion of the layer of conductive material to a level that will result in the conductivity type of the unmasked portion of the layer of conductive material being of the second conductivity type. A threshold adjust implant is then performed by implanting dopants of the second conductivity type material through the non-masked portion of the layer of conductive material and the underlying gate oxide layer into at least a portion of the first transistor region of the first conductivity type that will form the channel of the transistor to provide a threshold adjust therefor. After the threshold adjust implant, the gate electrode is patterned for both the first and second transistor regions such that a contiguous gate electrode is formed therebetween.

In another aspect of the present invention, the layer of conductive material is polycrystalline silicon which is formed by depositing polycrystalline silicon with a low pressure chemical vapor deposition (LPCVD) process in an atmosphere having a high concentration of high conductivity type impurities. The dopants that are introduced to change the impurity type of the unmasked portion of the polycrystalline silicon layer are diffused into the polycrystalline silicon layer.

In a yet further aspect of the present invention, after the contiguous gate electrode is formed, source/drain implants are formed into the first and second transistor regions on either side of the contiguous gate electrode to form source/drain regions.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
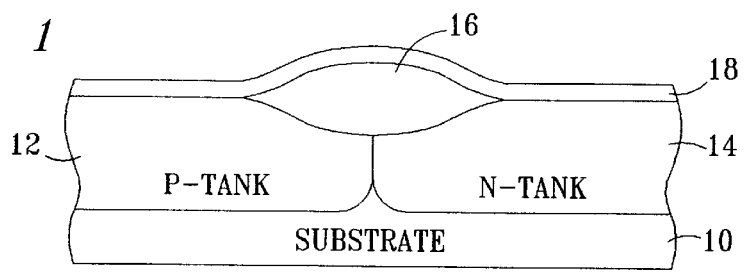
FIG. 1 illustrates a cross sectional view of a substrate after formation of the gate oxide layer.

Referring now to FIG. 1, there is illustrated a cross sectional diagram of a substrate 10 which has formed therein a P-tank 12 and an N-tank 14. These are formed with conventional techniques. Typically, this will require a self-aligned mask technique wherein an opening is made to expose one of the P-tank 12 or N-tank 14 and impurities of the appropriate conductivity type implanted therein, followed by subsequent masking of the implanted tank and exposing the other non-implanted tank. This is achieved by implanting therein impurities of the appropriate conductivity type. Thereafter, an isolation region 16 is formed between the two tanks which is a layer of field oxide material. This can either be formed with a LOCOS technique or a trench isolation technique, these being well known.

After formation of the P-tank 12, the N-tank 14 and the isolation region 16, a layer of gate oxide 18 is grown on the substrate to a thickness of between 20–100 Angstroms. This is a conventional technique.

Figure 2:
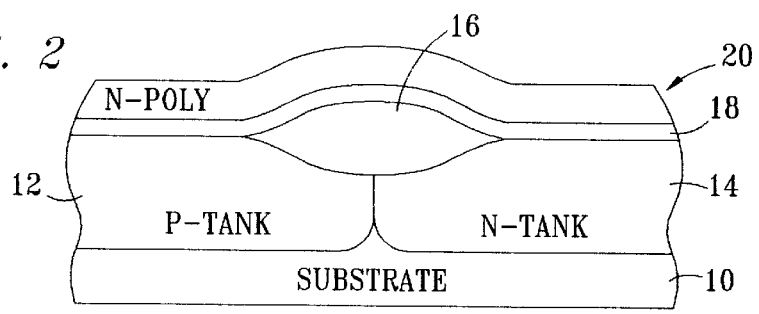
FIG. 2 illustrates a cross sectional diagram of the formation of the poly layer.
Figure 3:
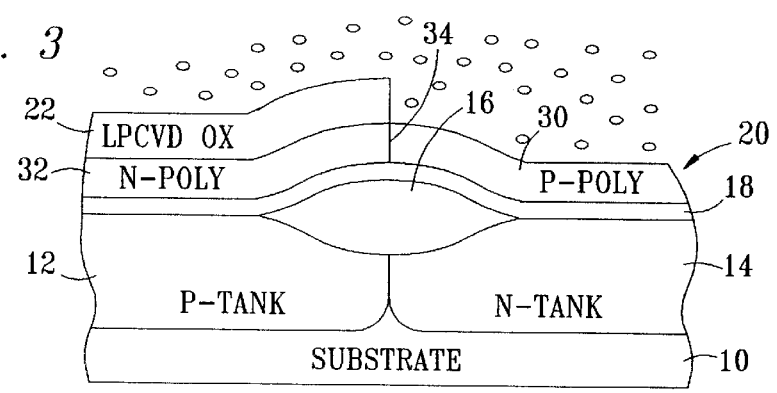
FIG. 3 illustrates a cross sectional diagram of the masking operation of the P-tank and diffusion of P-type impurities into the poly layer.

Referring now to FIG. 2, the next step of the process is illustrated. In this process, a layer of polysilicon 20 is deposited onto substrate 10 to a thickness of between 700–1,000 Angstroms. This is an N-type poly layer that is relatively thin as compared to that of a conventional logic gate. This is formed by depositing the polysilicon with a low pressure chemical vapor deposition (LPCVD) process wherein a gas such as phosphene is added to the process. This will result in the poly layer 20 being doped with an N-type material in an in-situ process. This will therefore not require a later ion implant step. After formation of the poly layer 20, this being a conformal layer, the next step is to form a thick oxide mask, as illustrated in the cross sectional view of FIG. 3. A layer of oxide 22 is deposited over the substrate with an LPCVD operation. Thereafter, the layer 22 is patterned and etched to remove the portion of the oxide layer 22 overlying the N-tank region 14 with a wet or dry etch. This is then followed by an annealing process wherein the substrate 10 is placed in an atmosphere of $B_2H_6$ gas or $B_2O_3$ at a temperature of 1,000–100° C. In this operation, sufficient P-type impurities will be diffused into the exposed portion of the poly layer 20 which will result in a counter-doped P-type poly region 30 and N-type poly region 32. The region 30 could also be formed utilizing ion implantation techniques. For example, the oxide layer 22 would function as an implant mask wherein the substrate would be subjected to an implant operation where $BF_2$ is implanted at an energy level sufficient to implant these P-type dopants beneath the surface of the exposed portion of the poly layer 20. The implant energy level is such that the dopants will not travel through the oxide mask 22 and into the underlying masked portion of the poly layer 20. The implant will result in a counter dopant concentration of approximately $1.0 \times 10^{-19}/cm^3$. A thermal anneal is then performed in the range of 880–1100° C. Of course, with either diffusion or implantation, there will be a junction 34 between the P-poly region 30 and the N-poly region 32.

Figure 4:
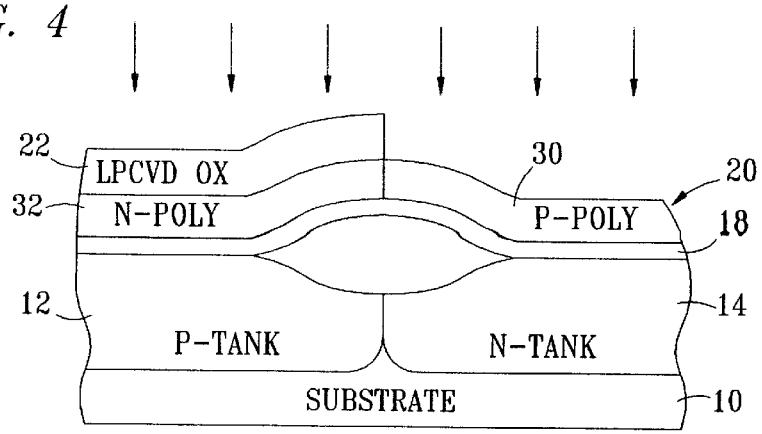
FIG. 4 illustrates the $V_T$ implant step.
Figure 5:
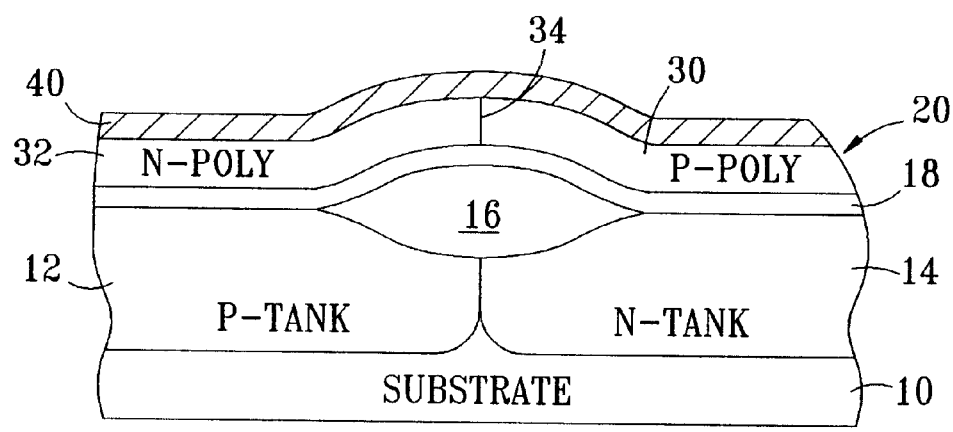
FIG. 5 illustrates a cross sectional diagram of the substrate after formation of a refractory metal silicide layer overlying the gate electrode layer.

After counter-doping of the poly layer 20 with the P-type impurities to form the P-type region 30 the substrate is subjected to a threshold adjust implant through the poly layer 20 and gate oxide layer 18, as illustrated in FIG. 4. This threshold adjust implant is performed in the N-type tank 14 associated with the P-channel transistors. This is implant essentially adjusts the level of impurities within the P-channel region for the P-channel transistor. These are P-type impurities which will increase the conductivity through the channel. With the process thus far described, it is noted that an advantage is provided in that the P-type poly region 30 is formed with a relatively simple diffusion with the mere addition an oxide mask. The mask that is utilized for the simple diffusion is also utilized for the threshold implant. As such, for the threshold implant required DRAM process, a $V_T$ implant mask is now saved. Therefore, both the doping of the P-type poly region 30 and the threshold implant are performed with the same mask.

After the $V_T$ implant is performed, the oxide layer 28 is removed with a wet etch process and the poly layer 20 has a layer of refractory metal silicide 40 formed thereon. This refractory metal silicide is formed by first sputtering a layer of refractory metal over the upper surface of the poly layer 20 followed by an anneal step at a temperature above 600° C. to react the refractory metal with the underlying silicon to form a refractory metal silicide. In one preferred embodiment, the refractory metal is tungsten (W) which will form a tungsten silicide (Wsi) layer.

Figure 6:
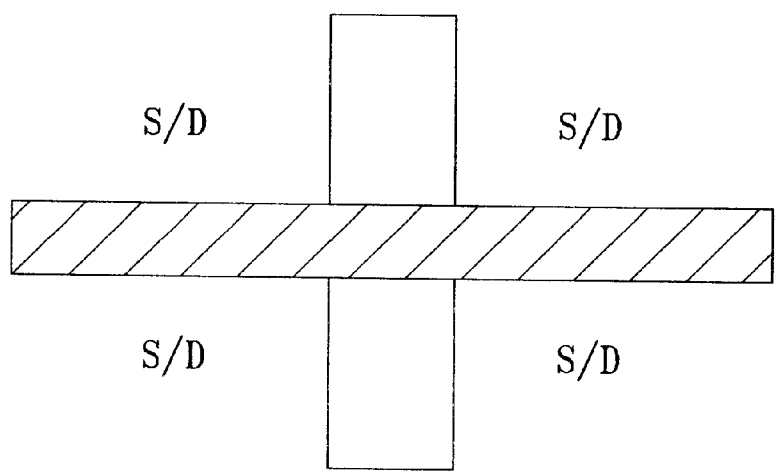
FIG. 6 illustrates a top view of the gate electrode after patterning thereof

After formation of the refractory metal silicide 40, the poly layer 20 and the refractory metal silicide layer 40 are patterned and etched to form the two gate electrodes, as illustrated in FIG. 6. However, it is noted that other processing (not shown) may be utilized to prevent diffusion of the P-type impurities from the region 30 and to the region 32 across junction 34. There are numerous processes for forming a barrier therebetween, such as etching a window therein and depositing a layer of metal nitride therein.

In summary, there has been disclosed a process for forming a dual-gate CMOS structure with a minimized number of steps. In this process, the poly layer is formed over the gate oxide layer in the two transistor regions, the P-channel transistor region and the N-channel transistor region. This poly layer is in-situ doped with N-type impurities. The region over the N-channel transistor is masked off with a layer of oxide, followed by diffusion of P-type impurities into the N-tank associated with the P-channel transistor. Utilizing the same mask, a threshold implant is performed in the P-channel transistor region.

Although the preferred embodiment has been described in detail, it should be understood that various changes, substitutions and alterations can be made therein without departing from the spirit and scope of the invention as defined by the appended claims.

What is claimed is:

1. A method for forming a gate electrode for a dual-gate CMOS transistor, comprising the steps of:

forming first and second transistor regions of first and second and opposite conductivity types, respectively, in which transistors are to be formed in a substrate;

forming a gate oxide layer over the surfaces of the first and second transistor regions in which channels of transistors to be formed therein are to be defined;

forming a layer of conductive material having in-situ dopants of the first conductivity type over the first and second transistor regions and above the gate oxide layer;

masking off the upper surface of the layer of conductive material overlying the second transistor region of the second conductivity type with a mask layer;

introducing dopants of the second conductivity type into the unmasked portion of the layer of conductive material to a level that will result in the conductivity type of the unmasked portion of the layer of conductive material being of the second conductivity type;

implanting dopants of the second conductivity type material through the non-masked portion of the layer of conductive material and the underlying gate oxide layer into at least the portion of the first transistor region of the first conductivity type that will form the channel of the transistor to provide a threshold adjust therefor, wherein the mask layer for the step of introducing dopants also provides the mask layer for the step of implanting; and patterning and defining a contiguous gate electrode between the first and second transistor regions.

2. The method of claim 1, wherein the first conductivity type material is N-type and the second conductivity type material is P-type.

3. The method of claim 1, wherein the layer of conductive material is a polycrystalline silicon layer.

4. The method of claim 3, wherein the polycrystalline silicon layer is a conformal layer.

5. The method of claim 3, wherein the polycrystalline silicon layer is formed with a step of depositing a polycrystalline silicon layer with a low pressure chemical vapor deposition (LPCVD) process in an atmosphere having a high concentration of first conductivity type impurities.

6. The method of claim 1, wherein the step of masking comprises the steps of:

depositing a layer of thick oxide with a low pressure chemical vapor deposition (LPCVD) process over the substrate; and patterning the layer of oxide to mask off the second transistor region of the second conductivity type material.

7. The method of claim 1, wherein the step of introducing dopants of the second conductivity type material into the layer of conductive material comprises diffusing the dopants of the second conductivity type into the layer of conductive material.

* * * * *